(12) United States Patent
Miller (10) Patent No.: US 12,042,607 B2
(45) Date of Patent: Jul. 23, 2024

(54) CATHETER WITH VALVES

(71) Applicant: Covidien LP, Mansfield, MA (US)

(72) Inventor: David J. Miller, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 1045 days.

(21) Appl. No.: 16/856,937

(22) Filed: Apr. 23, 2020

(65) Prior Publication Data
US 2021/0330933 A1 Oct. 28, 2021

(51) Int. Cl.
*A61M 25/00* (2006.01)
*A61F 2/00* (2006.01)

(52) U.S. Cl.
CPC ....... *A61M 25/0017* (2013.01); *A61F 2/0013* (2013.01); *A61M 25/0075* (2013.01); *A61M 2025/0076* (2013.01); *A61M 2205/3303* (2013.01); *A61M 2205/3331* (2013.01); *A61M 2210/1085* (2013.01)

(58) Field of Classification Search
CPC .. A61M 2025/0076; A61M 2205/3303; A61M 2205/3331; A61M 2210/1085; A61M 25/0017; A61M 25/0075; A61M 25/0026; A61M 2025/0002; A61M 25/007; A61M 25/10; A61M 25/04
See application file for complete search history.

(56) References Cited

U.S. PATENT DOCUMENTS 3,417,750 A * 12/1968 Carson .................. A61M 39/24
604/185
4,227,533 A * 10/1980 Godfrey ............ A61M 25/0075
604/266
4,704,102 A * 11/1987 Guthery ............ A61M 25/1025
604/921
4,813,935 A 3/1989 Haber et al.
5,085,636 A 2/1992 Burns
5,688,239 A * 11/1997 Walker .................. A61F 2/0022
604/27

(Continued)

FOREIGN PATENT DOCUMENTS

CN 103301514 A 9/2013
CN 203693875 U 7/2014

(Continued)

OTHER PUBLICATIONS

English translation of Wang (CN 110681032).*

(Continued)

*Primary Examiner* — Courtney B Fredrickson
(74) *Attorney, Agent, or Firm* — Fletcher Yoder, P.C.

(57) ABSTRACT

In some examples, a catheter includes an elongated body defining an injection lumen, a drainage lumen, and an inflation lumen. The elongated body includes an anchoring member positioned on a proximal portion of the elongated body. A sensor is positioned on a distal portion of the elongated body or distal to a distal end of the elongated body. The medical device includes an active valve positioned in or about the drainage lumen The active valve is configured to move between a closed state in which, when a proximal end of the elongated body is positioned in a bladder of a patient, the active valve is configured to retain fluid in the bladder, and an open state in which the active valve enables drainage of fluid from the bladder via the drainage lumen.

30 Claims, 5 Drawing Sheets

(56) References Cited

U.S. PATENT DOCUMENTS

| | | | |
|---|---|---|---|
| 6,470,213 B1 | 10/2002 | Alley | |
| 9,775,698 B2 | 10/2017 | Herrera et al. | |
| 10,188,396 B2 | 1/2019 | Folk et al. | |
| 10,433,790 B2 | 10/2019 | Ofek et al. | |
| 10,517,538 B2 | 12/2019 | Burnett et al. | |
| 10,542,923 B2 | 1/2020 | Chang et al. | |
| 2005/0015047 A1* | 1/2005 | Shah | A61M 25/1011 604/101.02 |
| 2010/0280451 A1* | 11/2010 | Teeslink | A61M 25/1011 604/99.04 |
| 2012/0016335 A1* | 1/2012 | Eshel | A61M 3/0208 604/500 |
| 2015/0280451 A1* | 10/2015 | Takeda | H02J 50/12 307/104 |
| 2017/0136209 A1* | 5/2017 | Burnett | A61B 5/0084 |
| 2018/0214297 A1 | 8/2018 | Hughett et al. | |
| 2019/0069831 A1 | 3/2019 | Kuck et al. | |
| 2019/0126006 A1 | 5/2019 | Rehm et al. | |
| 2019/0150801 A1 | 5/2019 | Suehara et al. | |
| 2019/0216401 A1 | 7/2019 | Brody | |
| 2019/0343445 A1 | 11/2019 | Burnett et al. | |
| 2020/0022636 A1 | 1/2020 | Suehara et al. | |
| 2020/0205718 A1* | 7/2020 | Silverton | A61B 5/1459 |

FOREIGN PATENT DOCUMENTS

| | | | | |
|---|---|---|---|---|
| CN | 204293573 U | | 4/2015 | |
| CN | 103598943 B | | 8/2016 | |
| CN | 209475348 U | | 10/2019 | |
| CN | 209679246 U | | 11/2019 | |
| CN | 110681032 A | * | 1/2020 | ........ A61M 25/0017 |
| GB | 2395128 A | * | 5/2004 | ........ A61B 5/14539 |
| GB | 2395128 A | | 5/2004 | |
| GB | 2448892 A | * | 11/2008 | ........ A61M 25/0017 |
| WO | 9007353 A1 | | 7/1990 | |
| WO | 03105942 A1 | | 12/2003 | |
| WO | 2018063499 A1 | | 4/2018 | |
| WO | 2019094591 A1 | | 5/2019 | |
| WO | 2019195028 A1 | | 10/2019 | |

OTHER PUBLICATIONS

ASTM International, "Standard Performance Specification for Foley Catheter", F623—19, Mar. 1, 2019, 10 pp.

International Preliminary Report on Patentability from International Application No. PCT/US2021/028440 dated Nov. 3, 2022, 13 pp.

International Search Report and Written Opinion of International Application No. PCT/US2021/028440, dated Sep. 14, 2021, 20 pp.

* cited by examiner

CATHETER WITH VALVES

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter that may be used for longer time periods than a non-Foley catheter. Some Foley catheters are constructed of silicon rubber and include an anchoring member, which may be an inflatable balloon, that may be inflated in a patient's bladder so a proximal end of the catheter does not slip out of the patient's bladder.

SUMMARY

In general, the disclosure describes a catheter (e.g., a Foley catheter), that includes at least one valve. The at least one valve is configured to affect a flow of a fluid or gas through a lumen, such as a drainage lumen, of the catheter. The drainage lumen may be configured to drain fluid from a bladder of a patient. In examples in which a catheter includes more than one valve, the valves may be positioned at different locations along a length of an elongated body of the catheter.

In some examples, the at least one valve includes an active valve positioned in the drainage lumen, where the active value is configured to affect the flow of a fluid or gas through the drainage lumen by at least selectively enabling and preventing the flow of a substance, such as urine or other fluid or gas, through the lumen. In some examples, in addition to or instead of the active valve, the at least one valve of the catheter includes a check valve positioned in a lumen, such as a drainage lumen, where the check valve is configured to affect the flow of a fluid or gas through the lumen by at least facilitating the flow of a fluid through the lumen while preventing flow of a substance, such as air, through the lumen.

In one example, this disclosure is directed to a catheter including an elongated body defining an injection lumen, a drainage lumen, and an inflation lumen, the elongated body comprising a proximal portion and a distal portion; an anchoring member positioned on the proximal portion of the elongated body, the anchoring member being fluidically coupled to the inflation lumen; and an active valve positioned in or about the drainage lumen, wherein the active valve is configured to move between a closed state in which, when a proximal end of the elongated body is positioned in a bladder of a patient, the active valve is configured to retain fluid in the bladder, and an open state in which the active valve enables drainage of fluid from the bladder via the drainage lumen.

In another example, this disclosure is directed to a method comprising: determining, by control circuitry, a condition has occurred; and in response to determining the condition has occurred, control an active valve of a catheter to open the active valve, the catheter comprising: an elongated body defining an injection lumen, a drainage lumen, and an inflation lumen, the elongated body comprising a proximal portion and a distal portion; an anchoring member positioned on the proximal portion of the elongated body, the anchoring member being fluidically coupled to the inflation lumen; and the active valve positioned in or about the drainage lumen, wherein the active valve is configured to move between a closed state in which, when a proximal end of the elongated body is positioned in a bladder of a patient, the active valve is configured to retain fluid in the bladder, and the open state in which the active valve enables the drainage of fluid from the bladder of the patient via the drainage lumen.

In a further example, this disclosure is directed to Foley catheter comprising: an elongated body defining an injection lumen, a drainage lumen, and an inflation lumen, the elongated body comprising a proximal portion and a distal portion; an anchoring member positioned on the proximal portion of the elongated body and fluidically coupled to the inflation lumen; a sensor positioned on the distal portion of the elongated body or distal to a distal end of the elongated body, the sensor configured to sense a substance of interest; a check valve positioned in or about the drainage lumen, the check valve being configured to prevent air from flowing through the drainage lumen; and an active valve positioned in or about the drainage lumen, the active valve being configured to move between a closed state in which, when a proximal end of the elongated body is positioned in a bladder of the patient, the active valve is configured to retain fluid in the bladder, and an open state in which the active valve enables drainage of the fluid from the bladder via the drainage lumen.

The details of one or more examples are set forth in the accompanying drawings and the description below. Other features, objects, and advantages will be apparent from the description and drawings, and from the claims.

DETAILED DESCRIPTION

Acute kidney injury (AKI) is a complication that may occur after some medical procedures, such as some cardiac surgeries, e.g., coronary artery bypass grafting (CABG). AKI may also occur after other surgeries that are lengthy and involve significant blood loss or fluid shifts. For example, a surgery patient's body may alter where their blood is directed which may lead to hypoxia of a kidney. A cause of surgery-associated AKI is hypoxia of the kidneys, which may cause an inflammatory response in a kidney of the patient. This inflammatory response may cause degradation of renal function of the patient. The degradation of renal function may cause an accumulation of waste products in the bloodstream, which may delay the patient's recovery from the surgery and lead to more extended hospital stays and may even lead to further complications.

While systemic vital signs like cardiac output, blood pressure, and hematocrit may be useful for monitoring the kidney function of a patient, it may also be useful to monitor the oxygenation status of the kidneys in order to limit, reduce the severity of, or even prevent the risk of AKI. Accurate monitoring of the oxygenation status of the kidneys can be challenging due to the inaccessibility of the kidneys. Near-Infrared spectroscopy (NIRS) measures regional oximetry, and has some utility in babies and relatively slender adults in measuring oxygenation of the kidneys, but may not have the depth of penetration and specificity required for some patients.

The present disclosure describes example medical devices, such as catheters, that are configured to monitor kidney function of patients, such as patients who are undergoing or who have undergone surgeries, which may help reduce occurrences of AKI. In some examples, the medical device includes at least one sensor configured to sense a parameter of a fluid of interest, such as urine in the case of kidney function monitoring. In some examples, the at least one sensor configured to sense a parameter of a fluid of interest may not be a part of the medical device, but be distal to a distal end of the medical device. In some examples, the medical device includes a sensor configured to sense bladder pressure, such as a pressure transducer.

While urine, bladders, and AKI are primarily referred to herein to describe the example medical devices, in other examples, the medical devices may be used with other target locations in a patient, such as intravascular locations, and to monitor fluids of interest other than urine and/or other patient conditions other than kidney function. In addition, while catheters are primarily referred to herein, in other examples, the medical device can have another configuration. As discussed in further detail below, in some examples, an example medical device includes a dissolved gas sensor, such as a dissolved oxygen sensor configured to sense an amount of oxygen dissolved in the urine (e.g., oxygen tension or uPO2 or PuO2) in the bladder and/or sense urine output (e.g., rate of urine production), from which a clinician or a device may be able to determine oxygenation status of the one or more kidneys of the patient. In some examples, the example medical device includes a bladder pressure sensor and/or a flow sensor, which provides sensed data to control circuitry for controlling an active valve.

Example parameters of interest sensed by a sensor described herein include, but are not limited to, any one or more of an amount of dissolved oxygen, urine concentration, urine electrical conductivity, urine specific gravity, urine biomarkers, amount of dissolved carbon dioxide in the urine, urine pH, bladder or abdominal pressure, bladder temperature, urine color, urine creatinine, or motion from an accelerometer or other motion sensor. In some cases, it may be desirable to sense one or more of these parameters relatively close to the kidneys as possible because when sensors are positioned further away from the kidneys, the risk of introducing noise or losing signal strength increases and/or the risk of the concentration or integrity of a substance of interest in the fluid of interest (e.g., urine) changing prior to being sensed by the sensor may increase. For example, an electrical, optical or radio frequency signal representative of a parameter sensed close to the kidneys, may be affected by noise and/or loss of signal strength as the signal travels from a sensor close to the kidneys to a device that may process the signal and display information regarding the sensed parameter. As another example, in the case of a Foley catheter, it may be desirable to sense one or more of these parameters at the proximal end of the Foley catheter (e.g., in the bladder of the patient). However, placing these sensors at the proximal end of the catheter may increase the size and stiffness of the catheter and, as a result, may undermine the patient comfort or deliverability of the catheter. By design, a Foley catheter is configured to be small and flexible, such that it can be inserted through the urethra and into the bladder of a patient. If a Foley catheter were stiffer, then it may be more difficult to comfortably insert the catheter into the bladder of the patient.

As used herein, "sense" may include detect and/or measure." As used herein, "proximal" is used as defined in Section 3.1.4 of ASTM F623-19, Standard Performance Specification for Foley Catheter. That is, the proximal end of a catheter is the end closest to the patient when the catheter is being used by the patient. The distal end is therefore the end furthest from the patient. In some examples, "prevent" may mean completely prevent or partially prevent (e.g., effectively prevent), such as by restricting, inhibiting, impeding, or hindering. For example, to prevent the flow of a substance through a lumen may mean that the substance may enter an end of the lumen but all of the substance may not exit the other end of the lumen.

The amount of dissolved oxygen in a patient's urine may be indicative of kidney function or kidney health. For example, dissolved oxygen in a patient's urine in the bladder may correlate to perfusion and/or oxygenation of the kidneys, which is indicative of kidney performance. However, dissolved oxygen can be relatively difficult to measure. One way to measure dissolved oxygen is by fluorescence or luminescence lifetime sensor(s). The decay of glow is indicative of the level of oxygen in a patient's urine. To more accurately measure the level of oxygen in a patient's urine, it may be desirable to take the measurement prior to any significant modification in the oxygen content in the urine, e.g., as close to the kidneys as possible. However, it may not be feasible to place a dissolve oxygen sensor at the proximal end of the catheter as doing so may increase cost, size, and flexibility of the catheter.

Some Foley catheters include an elongated body made from a silicone rubber that is porous to oxygen. Thus, as a fluid flows through a drainage lumen of the Foley catheter from a proximal opening to the drainage lumen to a distal opening to the drainage lumen, some oxygen may dissipate through the walls of the elongated body and into a surrounding environment. To minimize the loss of oxygen or other substance of interest in other examples in such a manner, it may be desirable to minimize transit time of urine (or other fluid) from the bladder of a patient to a sensor on the distal portion of such a Foley catheter or distal to a distal end of the Foley catheter. Slower fluid transit times through the catheter lumen may result in erroneous or skewed measurements as the oxygen may dissipate from the urine through the walls of the Foley catheter as the urine travels from the bladder through the lumen. Oxygen may also permeate into the urine through the walls of the Foley catheter as the urine travels through the lumen from the bladder to sensor. For example, the oxygen may dissipate into or permeate from other tissues in or near the urinary tract and the atmosphere outside of the urinary tract. The catheters described herein enable a sensor to sense a substance of interest in a fluid despite being positioned relatively far away from the fluid source, such as a bladder.

In accordance with examples of this disclosure, rather than integrating all of the desired sensors in the proximal portion of an elongated body of a catheter (e.g., the portion that is to be inserted into the bladder of the patient or otherwise introduced in a patient), one or more sensors may be positioned anywhere along the elongated body (e.g., on the proximal portion or a distal portion) or distal to a distal end of the elongated body. The distal portion of the elongated body may include, for example, the portion intended to remain outside of the patient when the proximal portion is introduced in the patient. By locating sensors at the distal portion of the catheter or distal to a distal end of the elongated body, the sensors may be larger, may rely upon relatively more electrical and/or optical connections and the catheter itself may be smaller and more flexible than it would have been had all the sensors been positioned at the proximal portion of the catheter.

An active valve may be located in or about a lumen of an elongated body of the catheter and is configured to prevent the flow of a fluid, such as urine, through the lumen to a distal opening when closed and enable the flow of the fluid through the lumen to the distal opening when opened. The active valve may be used to reduce transit time of a fluid through the catheter, thereby reducing the time with which the draining fluid may be in contact with a porous material of the elongated body. For example, a catheter, when introduced in a patient such that a proximal opening to the lumen is within the bladder, prevents or substantially limits fluid from exiting the bladder while the active valve is closed, thereby keeping bladder pressure relatively high while the active valve is closed. When an oxygen measurement is desired, the active valve may be opened to enable the flow of urine out of the bladder via the lumen of the elongated body. The relatively high bladder pressure created by the closure of the active valve may result in a relatively continuous fluid flow through the lumen of the elongated body compared to examples in which fluid is permitted to exit the bladder through the lumen more organically (without an active valve controlling the fluid flow). As fluid leaves the bladder, the last of the fluid to drain through the lumen (e.g., the last 25 percent or so) may be the fluid that most recently exited the kidneys and may be most representative of the oxygen in the kidneys relative to the fluid that initially flowed out of the bladder. For example, the last volume of fluid exiting the kidneys may have an oxygenation closest to the oxygenation of the kidneys. In this manner, a dissolved oxygen sensor located on a distal portion of a catheter according to the techniques of this disclosure or distal to the distal end of a catheter according to the techniques of this disclosure may provide a more accurate measurement of the dissolved oxygen content of the kidneys than with a traditional Foley catheter that does not include an active valve in a drainage lumen.

In some examples, the catheter further includes a check valve located in or about a lumen of the elongated body and configured to prevent the flow of air through the lumen. The check value may prevent mixing of the fluid in the lumen with air by preventing the flow of air through the lumen. The check valve can be, for example, a one-way valve configured to permit fluid flow in a distal direction through the lumen and prevent fluid flow in a proximal direction through the lumen.

In some examples according to this disclosure, the medical device may be a Foley catheter having three or more lumens. The three or more lumens may include an inflation lumen, an injection lumen, and a drainage lumen. The active valve may be located in or about the drainage lumen. The inflation lumen may be configured to transport an inflation fluid from an inflation opening on a distal portion of the Foley catheter to an anchoring member of the Foley catheter. The anchoring member may be configured to hold the Foley catheter in place, such that the proximal end of the Foley catheter remains in the bladder of a patient when the anchoring member is deployed. The injection lumen may be configured to transport a first fluid from a fluid opening on the distal portion of an elongated body of the Foley catheter to a fluid opening on the proximal portion of the elongated body. The first fluid may exit the injection lumen at a fluid opening on the proximal portion of the elongated body and enter the patient's bladder. The drainage lumen may be configured to transport a second fluid, such as urine, the first fluid or a mixture thereof, from a fluid opening (to the drainage lumen) on the proximal portion of elongated body to a fluid opening (to the drainage lumen) on the distal portion of the elongated body. The active valve may be opened when or after the first fluid is injected, which may cause a reduction in the transit time of the second fluid from the bladder of the patient to one or more sensors on the distal portion of the catheter or distal to the distal end of the catheter. In some examples, a check valve may be located in the drainage lumen which may prevent air from traveling through the drainage lumen and mixing with the second fluid.

Introducing the first fluid into the bladder of a patient via the injection lumen when the active valve in the drainage lumen is closed may help to control the bladder pressure and achieve a desired bladder pressure. When an oxygen measurement is desired, the active valve may be opened, for example, in response to manual input by a clinician or automatically under the control of control circuitry. In some examples, the control circuitry may control the opening and closing of the active valve in the drainage lumen based on sensor input (such as input from a bladder pressure sensor or a flow sensor), a time (e.g., as described below), clinician input, or other control parameters or combinations thereof. For example, the control circuitry may open the active valve when a sensed bladder pressure reaches a predetermined level, e.g., 5 mmHg or higher. Control circuitry may also close the active valve when the sensed bladder pressure reaches a lower predetermined level, for example 0.25 mmHg, when a flow sensor senses a relatively low flow rate or senses the flow becoming negative. In addition or instead, the control circuitry may open the active valve after a predetermined amount of time has passed from when the catheter was inserted, from when the active valve was last closed or from when the active valve was last opened. In some examples, the predetermined amount of time may be input to the control circuitry by a clinician. In another example, a clinician may provide input (e.g., by pressing a button, touching a touchscreen, clicking a mouse, speaking a command, or some other user input) to the control circuitry to cause the control circuitry to open the active value.

Figure 1:
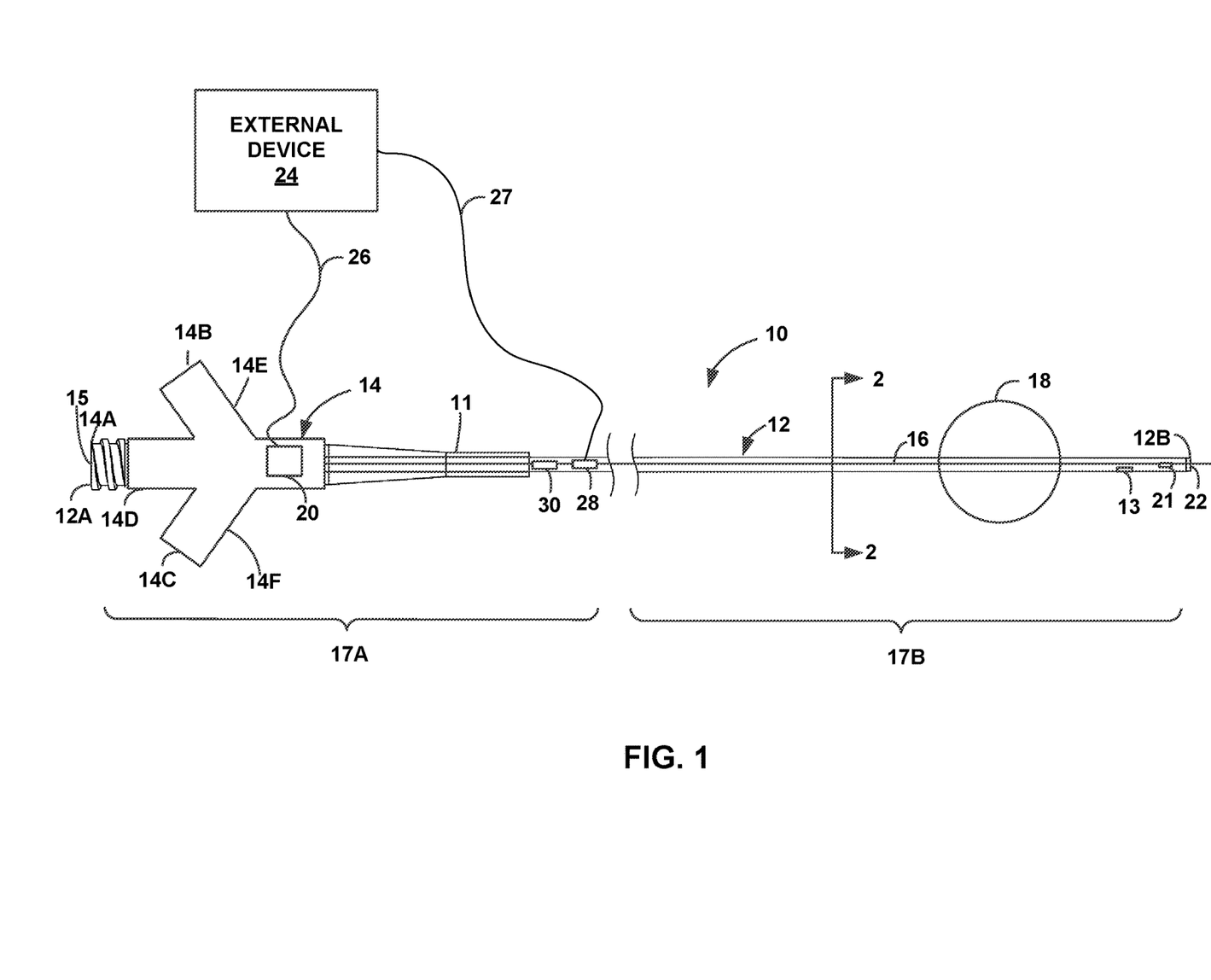
FIG. 1 is a diagram illustrating an example catheter including a check valve and an active valve.

FIG. 1 is a conceptual side elevation view of an example catheter 10, which includes elongated body 12, hub 14, and anchoring member 18. In some examples, catheter 10 is a Foley catheter. While a Foley catheter and its intended use are primarily referred to herein to describe catheter 10, in other examples, catheter 10 can be used for other purposes, such as to drain wounds or for intravascular monitoring or medical procedures.

Catheter 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., such that proximal end 12B of elongated body 12 is within the patient's bladder, distal portion 17A may remain outside of the body of the patient.

Elongated body 12 is a structure (e.g., a tubular structure) that extends from distal end 12A to proximal end 12B and defines one or more inner lumens. In the example shown in FIGS. 1-2, elongated body 12 defines injection lumen 32, drainage lumen 34 and inflation lumen 36 (shown in FIG. 2). In some examples, drainage lumen 34 may be configured to drain a fluid from a target site, such as a bladder. In other examples drainage lumen 34 may be used for any other suitable purpose, such as to deliver a substance or another medical device to a target site within a patient. Drainage lumen 34 may extend from proximal fluid opening 13 to distal fluid opening 14A. Both fluid opening 13 and fluid opening 14A may be fluidically coupled to drainage lumen 34, such that a fluid may flow from one of fluid opening 13 or fluid opening 14A to the other of fluid opening 13 or fluid opening 14A through drainage lumen 34. Fluid opening 13 and fluid opening 14A may also be referred to as drainage openings.

In some examples, injection lumen 32 (shown in FIG. 2) may be an injection lumen configured to deliver a fluid to a target site, such as a bladder. In other examples, injection lumen 32 may be used for any other suitable purpose, such as to deliver a medical device to a target site within a patient. Injection lumen 32 may extend from distal fluid opening 14C to proximal fluid opening 22. Both fluid opening 14C and fluid opening 22 may be fluidically coupled to injection lumen 32, such that a fluid may flow from one of fluid opening 14C or fluid opening 22 to the other of fluid opening 14C or fluid opening 22 through injection lumen 32. In the example where injection lumen 32 is an injection lumen, fluid opening 14C and fluid opening 22 may be injection openings. While fluid opening 22 is shown at the proximal end 12B of elongated body 12, fluid opening 22 may be positioned elsewhere on proximal portion 17B proximal to anchoring member 18.

Inflation lumen 36 (shown in FIG. 2) is configured to transport a fluid, such as sterile water or saline, or a gas, such as air, from inflation opening 14B to anchoring member 18. For example, an inflation device (not shown) may pump fluid or gas into inflation lumen 36 through inflation opening 14B into anchoring member 18 such that anchoring member 18 is inflated to a size suitable to anchor catheter 10 within the patient's bladder. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A, fluid opening 14C and an opening 14B via which a clinician may access the deployment mechanism.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal portion 17A and proximal portion 17B of elongated body 12 may each have any suitable length.

In the example shown in FIG. 1, distal end 12A of elongated body 12 is received within hub 14 and is mechanically connected to hub 14 via an adhesive, welding, or another suitable technique or combination of techniques. Hub 14 is positioned at a distal end of elongated body 12 and defines an opening through which the one or more inner lumens (e.g., injection lumen 32, drainage lumen 34 and inflation lumen 36, shown in FIG. 2) of elongated body 12 may be accessed and, in some examples, closed. While hub 14 is shown in FIG. 1 as having three arms, 14D, 14E and 14F, hub 14 may have any suitable number of arms, which may depend on the number of inner lumens defined by elongated body 12. For example, each arm may be fluidically coupled to a respective inner lumen of elongated body 12. In the example of FIG. 1, hub 14 comprises a fluid opening 14A, which is fluidically coupled to drainage lumen 34, an inflation opening 14B, which is fluidically coupled to inflation lumen 36, and a fluid opening 14C which is fluidically coupled to injection lumen 32 (shown in FIG. 2) of elongated body 12. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A, fluid opening 14C and an opening 14B via which a clinician may access the deployment mechanism.

In examples in which catheter 10 is a Foley catheter, a fluid collection container (e.g., a urine bag) may be attached to fluid opening 14A for collecting urine draining from the patient's bladder. Inflation opening 14B may be operable to connect to an inflation device to inflate anchoring member 18 positioned on proximal portion 17B of catheter 10. Anchoring member 18 may be uninflated or undeployed when not in use. Hub 14 may include connectors, such as connector 15, for connecting to other devices, such as the fluid collection container and the inflation source. Fluid opening 14C may be operable to connect to an injection device (not shown), such as a pump, for injecting fluid into the patient's bladder. In some examples, catheter 10 includes strain relief member 11, which may be a part of hub 14 or may be separate from hub 14.

Sensor 20 may be positioned on distal portion 17A, such as on hub 14. In some examples, sensor 20 is alternatively positioned distal to distal end 12A. Sensor 20 may be configured to sense a parameter of interest, such as dissolved oxygen, in a fluid, such as urine.

Proximal portion 17B of catheter 10 comprises anchoring member 18, fluid opening 13, fluid opening 22 and, in some examples, sensor 21. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 can include an anchor balloon or other expandable structure. When inflated or deployed, anchoring member 18 may function to anchor catheter 10 to the patient, for example, within the patient's bladder. In this manner, the portion of catheter 10 on the proximal side of anchoring member 18 may not slip out of the patient's bladder. Fluid opening 13 may be positioned on the surface of elongated body 12 between anchoring member 18 and the proximal end 12B (as shown) or may be positioned at the proximal end 12B. Fluid opening 22 may be positioned at the proximal end 12B (as shown) of elongated body 12 or may be positioned on the surface of elongated body between anchoring member 18 and the proximal end 12B.

Catheter 10 includes an active valve 28 positioned in or about drainage lumen 34 (shown in FIGS. 2-3B) and configured to move between a closed state and an open state.

Active valve 28 is configured to enable drainage of fluid (e.g., urine) through drainage lumen 34 when in the open state and retain fluid, for example, in the bladder of a patient when in the closed state. For example, active valve 28 may prevent (e.g., completely prevent or substantially limit) the flow of the fluid from proximal fluid opening 13 through drainage lumen 34 to distal fluid opening 14A from when in the closed state. Active valve 28 may be a gate valve, a globe valve, a plug valve, a ball valve, a butterfly valve, a diaphragm valve, a pinch valve, a needle valve or any type of valve that may enable the flow of a fluid through drainage lumen 34 when open and prevent the flow of the fluid through drainage lumen 34 when closed. Active valve 28 is discussed further later in this disclosure with respect to FIGS. 3A-3B.

Active valve 28 may be opened and closed based on preset time intervals, based on sensor readings (e.g., sensor data indicative of a bladder condition such as bladder pressure readings from sensor 21), as triggered by a clinician, or by any other manner. For example, control circuitry 210 (FIG. 3) of external device 24 may include control circuitry configured to open and close active valve 28 based on one or more of a time, sensor data, clinician input or the like. For example, control circuitry 210 may receive sensor data indicative of a bladder condition, such as bladder pressure, and may open the active valve when a sensed bladder pressure sensed by sensor 21 reaches a predetermined level. Sensor 21 may communicate sensor data to external device 24 via an electrical, optical, wireless or other connection. In some examples, sensor 21 may communicate sensor data to external device 24 through a connection(s) within elongated body 12 of catheter 10 from proximal portion 17B to distal portion 17A via embedded wire(s) or optical cable(s). In other examples, sensor 21 may communicate sensor data to external device 24 via a wireless communication technique. Sensor 21 is mechanically connected to elongated body 12 or another part of catheter 10 using any suitable technique, such as, but not limited to, an adhesive, welding, by being embedded in elongated body 12, via a crimping band or another suitable attachment mechanism or combination of attachment mechanisms.

In addition or instead of using sensed bladder pressure to control the opening and closing of active valve 28, control circuitry 210 may open active valve 28 after a predetermined amount of time has passed from when the catheter was inserted, from when active valve 28 was last closed or from when active valve 28 was last opened. In some examples, the predetermined amount of time may be input to the control circuitry 210 by a clinician. In another example, a clinician may interact with user interface 204 (FIG. 3) of external device 24 (e.g., by pressing a button, touching a touchscreen, clicking a mouse, speaking a command, or provide some other physical or audible input) and control circuitry 210 may receive the user input and open the active value.

In examples in which catheter 10 is a Foley catheter, when active valve 28 in a closed position and catheter 10 is positioned in the patient such that proximal fluid opening 13 is in the bladder of the patient, active valve 28 prevents urine from draining from the bladder via drainage lumen 34. As a result, urine may accumulate in the bladder and a pressure in the bladder increases over time. Opening active valve 28 may lower the bladder pressure and enables urine from the bladder to drain from the bladder via drainage lumen 34 and out distal fluid opening 14A. As the urine previously stored in the bladder drains through drainage lumen 34, sensor 20 can measure the amount of oxygen in the urine, e.g., continuously or less frequently, and processing circuitry 200 may record a value from sensor 20 in memory 202 at the end of the flow that may be indicative of the dissolved oxygen content in urine most recently out of the kidneys and therefore the most accurate measurement of the oxygen in the kidneys. While active valve 28 is shown located on the distal portion 17A of elongated body 12, active valve 28 may be located anywhere along elongated body 12, such as on distal portion 17A or proximal portion 17B.

In the example of FIG. 1, distal portion 17A of catheter 10 includes check valve 30 and sensor 20. Check valve 30 may be positioned in or about drainage lumen 34 (shown in FIGS. 2-3B). In examples in which catheter 10 is a Foley catheter, check valve 30 may be configured to minimize the amount of air entering drainage lumen 34 or even prevent air from entering drainage lumen 34. For example, check valve 30 may allow urine flow out of drainage lumen 34, but not allow reverse flow or the flow of air through drainage lumen 34. If air enters drainage lumen 34 of a Foley catheter, then the air may cause vapor lock and inconsistent, noisy urine sensor measurements as the air may mix with draining fluid. By minimizing or preventing air from entering drainage lumen 22, check valve 30 may provide for more reliable and consistent sensor data. For example, check valve 30 may aid the reliability of sensor 20 by ensuring that sensor 20 is surrounded by fluid and not a mixture of fluid and air. Check valve 30 may have any suitable configuration. For example, check valve 30 can include a duckbill valve, a swing valve, a ball valve, a diaphragm valve, an umbrella valve, or any other type of check valve. While in the example of FIG. 1, check valve 30 is shown as positioned on distal portion 17A of elongated body 12, check valve 30 may be positioned anywhere on elongated body 12, such as on distal portion 17A or proximal portion 17B.

Sensor 20 is configured to sense a substance of interest, for example dissolved oxygen, in a fluid, such as urine. Sensor 20 may be positioned on hub 14, as shown, or may be positioned elsewhere on distal portion 17A of the body of catheter 10, or may be positioned distal to distal end 12A, e.g., on tubing connected to a fluid collection container (e.g., a urine bag) or the like. Sensor 20, may be one or more sensors that are relatively larger, require relatively more electrical or optical connections, than sensors that could be located on the proximal portion 17B. While sensor 20 is primarily discussed herein as sensing dissolved oxygen (oxygen tension or uPO2) and/or fluid output, in some examples, sensor 20 may include sensor(s) configured to sense temperature, pressure, fluid concentration, amount of dissolved carbon dioxide in the fluid, fluid pH, fluid color, fluid creatinine, and/or motion.

In some examples, sensor 20 is mechanically connected to elongated body 12 or another part of catheter 10 using any suitable technique, such as, but not limited to, an adhesive, welding, by being embedded in elongated body 12, via a crimping band or another suitable attachment mechanism or combination of attachment mechanisms. As discussed above, in some examples, sensor 20 is not mechanically connected to elongated body 12 or catheter 10, but is instead mechanically connected to a structure that is distal to a distal end of catheter 10, such as to tubing that extends between hub 14 and a fluid collection container.

Sensor 20 may be configured to communicate sensor data to an external device 24. External device 24 may be a computing device, such as a workstation, a desktop computer, a laptop computer, a smart phone, a tablet, a server or any other type of computing device that may be configured to receive, process and/or display sensor data. Sensor 20 may communicate sensor data to the external device via a connection 26. In some examples, external device 24 may control active valve 28 via connection 26 or via a separate connection 27. Connection 26 or connection 27 may be an electrical, optical, wireless or other connection.

Although only sensor 20 and sensor 21 are shown in FIG. 1, in other examples, catheter 10 can include any suitable number of sensors on proximal portion 17B and any suitable number of sensors on distal portion 17A, where the sensors on proximal portion 17B sense the same or different parameters and the sensors on distal portion 17A sense the same or different parameters. In addition, some or all of the sensors on proximal portion 17B can sense the same or different parameters as the sensors on distal portion 17A. For example, in the case where sensors on the distal portion may be temperature dependent, it may be desirable to sense temperature both on the proximal portion 17B and the distal portion 17A.

Elongated body 12 may be structurally configured to be relatively flexible, pushable, and relatively kink- and buckle-resistant, so that it may resist buckling when a pushing force is applied to a relatively distal portion of the medical device to advance the elongated body proximally through the urethra and into the bladder. Kinking and/or buckling of elongated body 12 may hinder a clinician's efforts to push the elongated body proximally.

In some examples, rather than being formed from two or more discrete and separate longitudinally extending segments that are mechanically connected to each other, e.g., at axial butt joints, elongated body 12 may be substantially continuous along a length of elongated body 12. A substantially continuous elongated body 12 may be better configured to distribute forces in a longitudinal direction (in a direction along longitudinal axis 16) and rotational direction (rotation about longitudinal axis 16) compared to an elongated body including two or more longitudinally extending segments that are mechanically connected to each other. Thus, the substantially continuous construction of elongated body 12 may contribute to the ability of elongated body 12 to transfer axial pushing forces from distal portion 17A of elongated body 12 to proximal portion 17B, as well transfer rotational forces (if any) applied from distal portion 17A of elongated body 12 to proximal portion 17B.

In some examples, at least a portion of an outer surface of elongated body 12 includes one or more coatings, such as an anti-microbial coating, and/or a lubricating coating. The lubricating coating may be configured to reduce static friction and/ kinetic friction between elongated body 12 and tissue of the patient as elongated body 12 is advanced through the urethra.

Figure 2:
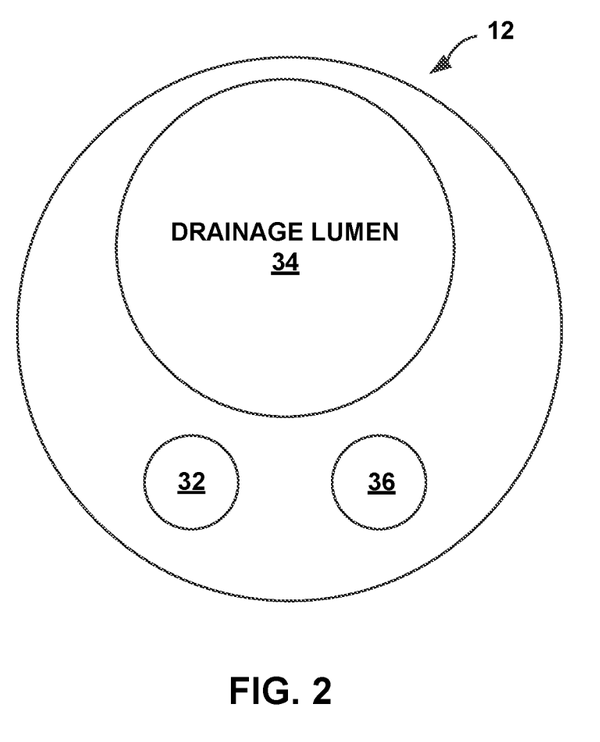
FIG. 2 is a diagram illustrating an example cross-sectional view of the catheter of FIG. 1, the cross-sections being taken along lines 2-2 of FIG. 1.

FIG. 2 is a diagram illustrating an example cross-section of elongated body 12 of catheter 10, where the cross-section is taken along line 2-2 in FIG. 1 in a direction orthogonal to central longitudinal axis 16. FIG. 2 depicts a cross section of elongated body 12, which defines injection lumen 32, drainage lumen 34, and inflation lumen 36. While injection lumen 32, drainage lumen 34, and inflation lumen 36 are shown as circular in cross-section, they may have any suitable cross-sectional shape in other examples.

Elongated body 12 can define any suitable number of lumens. For example, although one inflation lumen 36 is shown in FIG. 2, in other examples, elongated body 12 can define a plurality of inflation lumens 36, e.g., that are distributed around injection lumen 32 or drainage lumen 34. As another example, anchoring member 18 may be an expandable structure that is not an inflatable balloon. In such examples, inflation lumen 36 may be replaced by a deployment mechanism which may permit a clinician to expand the expandable structure. For example, inflation lumen 36 may be replaced by a mechanical device that may be pushed and pulled separately from the catheter 10 by a clinician to expand or retract the expandable structure. As another example of a different lumen configuration, in some examples, elongated body 12 may not include injection lumen 32 and can have only drainage lumen 34 and inflation lumen 36.

Figure 3:
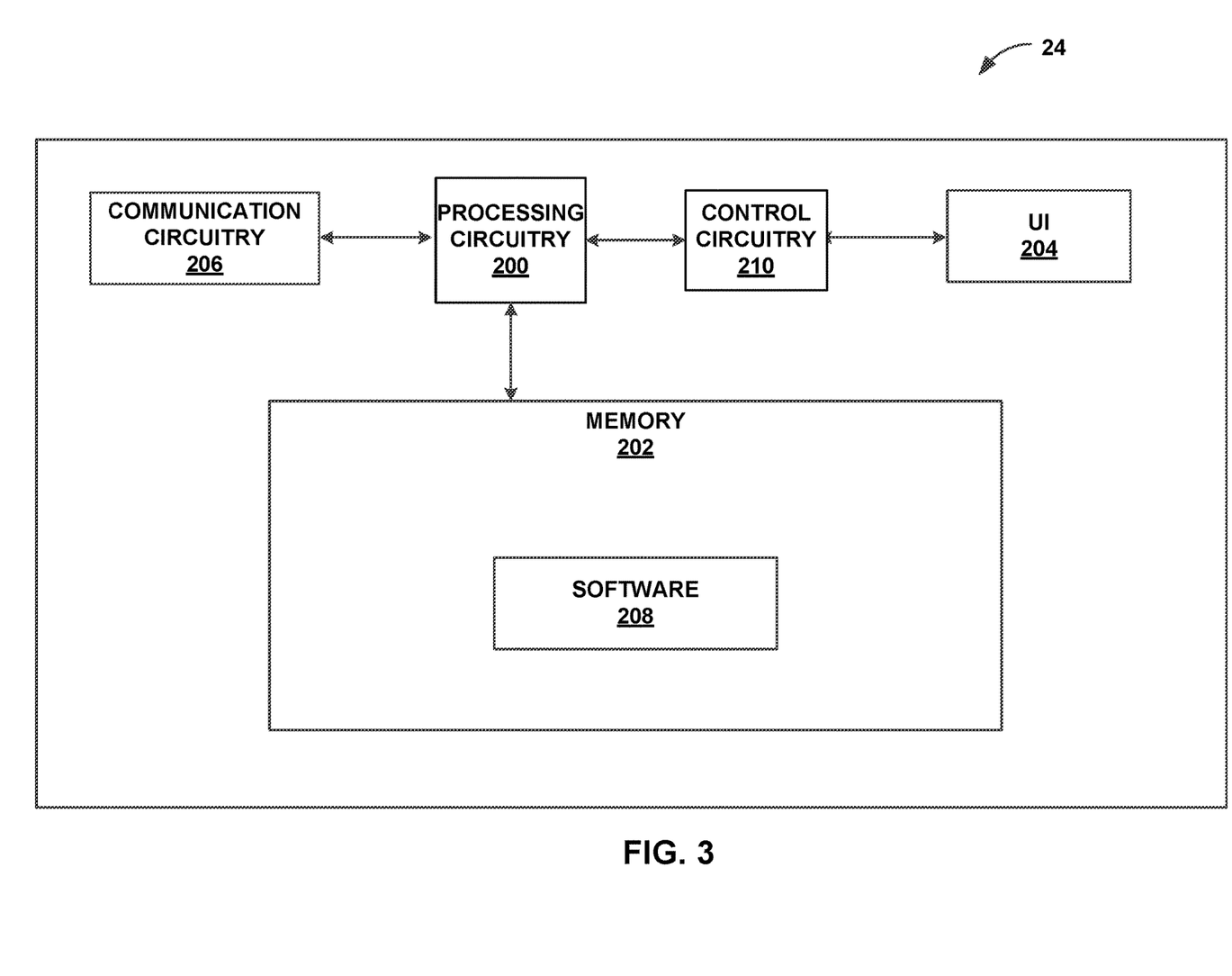
FIG. 3 is a block diagram of an example external device that may be used with a medical device according to example techniques of this disclosure.

FIG. 3 is a functional block diagram illustrating an example of an external device 24 configured to communicate with sensor 20, receive information from sensor 20 and control active valve 28. In some examples, external device also is configured to communicate with or receive information from sensor 21. In the example of FIG. 3, external device 24 includes processing circuitry 200, control circuitry 210 for controlling active valve 28, memory 202, user interface (UI) 204, and communication circuitry 206. In some examples, processing circuitry 200 may include control circuitry 210. External device 24 may be a dedicated hardware device with dedicated software for the reading sensor data. Alternatively, external device 24 may be an off-the-shelf computing device, e.g., a desktop computer, a laptop computer, a tablet, or a smartphone running a mobile application that enables external device 24 to read sensor data from sensor 20.

In some examples, a user of external device 24 may be clinician, physician, or heath care giver. In some examples, a user uses external device 24 to monitor a patient's kidney function. In some examples, a user uses external device 24 to control active valve 28. In some examples, the user may interact with external device 24 via UI 204, which may include a display to present a graphical user interface to the user, and a keypad or another mechanism (such as a touch sensitive screen) for receiving input from the user. External device 24 may communicate with sensor 20, sensor 21 or with active valve 28 using wired, wireless or optical methods through communication circuitry 206. For example, processing circuitry 200 of external device 24 may process sensor data from sensor 20 or sensor 21. Control circuitry 210 may control active valve 28 to open and to close based on one or more of a time, sensor data (such as bladder pressure data from sensor 21), or clinician input.

Processing circuitry 200 and control circuitry 210 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 200 or control circuitry may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, such as software 208, which may include one or more program modules, which are executable by processing circuitry 200 or control circuitry 210. When executed by processing circuitry 200, such program instructions may cause processing circuitry 200 or control circuitry 210, and external device 24 to provide the functionality ascribed to them herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Figure 4:
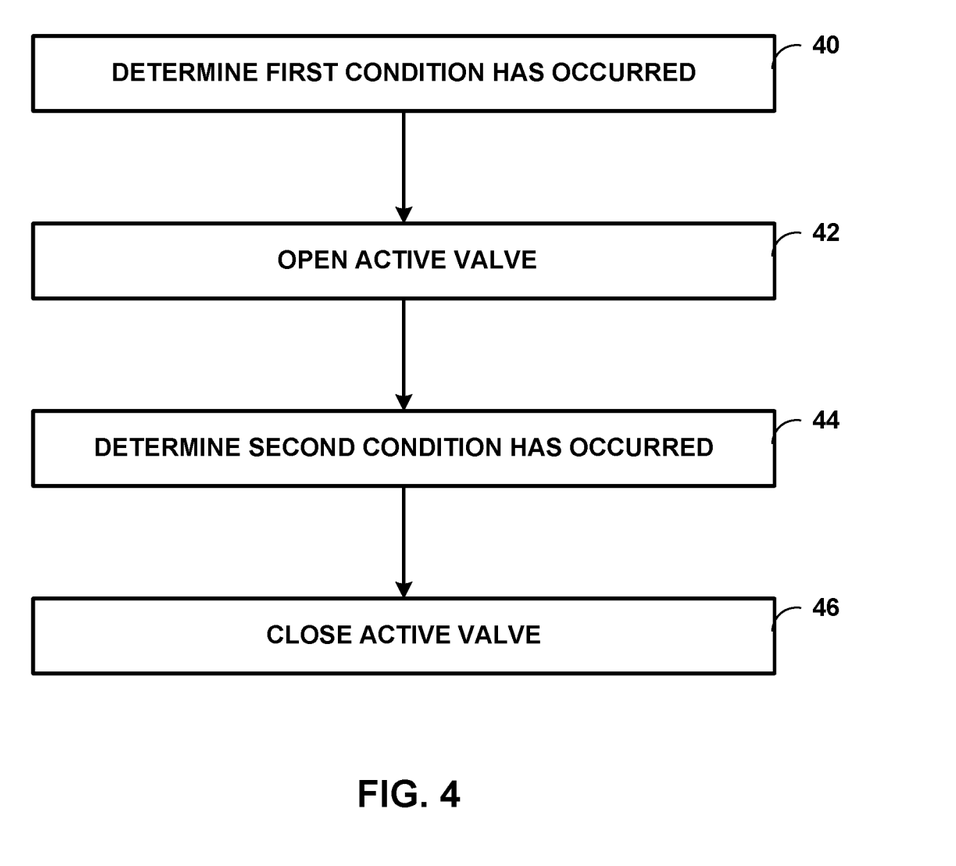
FIG. 4 is a flowchart illustrating an example method of operating a catheter according to example techniques of this disclosure.

FIG. 4 is a flowchart illustrating an example operation of catheter 10 after catheter 10 is inserted such that proximal end 12B of elongated body 12 is positioned in a bladder of a patient and, for example, elongated body 12 extends through a urethra of the patient. In some examples, active valve 28 is initially in a closed position when catheter 10 is inserted into the patient. In accordance with the technique shown in FIG. 4, control circuitry 210 determines whether a first condition has occurred (40). For example, control circuitry 210 may determine a sensed parameter, such as bladder pressure which may be sensed by sensor 21, has is greater than or equal to a first predetermined threshold. The first predetermined threshold as well as other thresholds described herein may be stored in memory 202 (FIG. 3) of external device 24 or a memory of another device. In other examples, control circuitry 210 may determine the first condition has occurred based on a time. For example, control circuitry 210 may determine a first predetermined period of time has passed since catheter 10 was inserted in the patient, the last time active valve 28 was closed or the last time the active valve was opened. In other examples, control circuitry 210 may determine that a user has provided an indication, e.g., through user interface 204, to open active valve 28, such as through a button push, a touchscreen touch, a mouse click, a voice command, or some other input. In response to determining the first condition occurred, control circuitry 210 controls active value 28 to open (42), e.g., by sensing sending a first signal to open active valve 28.

Active valve 28 may open in response to the first signal permitting the flow of a fluid from, e.g., fluid opening 13, through a lumen such as drainage lumen 34, to a fluid opening at the distal end of the catheter, such as fluid opening 14A. The opening of active valve 28 may result in a reduced transit time of the fluid through the lumen when compared with the transit time of the fluid through a conventional Foley catheter that does not include an active valve controlling fluid flow through a drainage lumen. The reduced transit time may result in less of a substance of interest permeating the relatively porous to the substance of interest material of elongated body 12. This reduced transit time may therefore enable a more accurate sensing of the substance of interest in the fluid, such as dissolved oxygen, by sensor 20 (FIG. 1).

In some examples, catheter 10 further includes check valve 30 configured to prevent air from flowing through the lumen, such as drainage lumen 34. By preventing air from flowing through the lumen, check valve 30 may prevent air from mixing with the fluid in the lumen which may further enable a more accurate sensing of the substance of interest in the fluid.

Control circuitry 210 can also control the closure of active valve 28. For example, as shown in FIG. 4, in some examples, control circuitry 210 determines whether a second condition has occurred (44). For example, control circuitry 210 may determine that a sensed parameter, such as bladder pressure which may be sensed by sensor 21, is less than the first predetermined threshold or less than or equal to a second predetermined threshold different from the first predetermined threshold. The sensed parameter less than the first predetermined threshold or less than or equal to the second predetermined threshold can indicate, for example, a sufficient amount of fluid has exited the bladder via drainage lumen 34 to enable sensor 20 to sense the parameter of interest in the urine or can indicate that the bladder is relatively empty.

In addition to or instead of determining the second condition has occurred based on the sensed parameter, control circuitry 210 may determine a predetermined period of time has passed since active valve 28 was last opened. For example, the predetermined period of time may be sufficient to enable the patient's bladder to drain enough to enable sensing of the substance of interest by sensor 20 in fluid recently exiting the kidneys. In other examples, processing circuitry 200 may determine that a clinician has provided an indication to close active valve 28, such as through a button push, a touchscreen touch, a mouse click, a voice command, or some other input provided via user interface 204, for example. In response to determining the second condition has occurred, processing circuitry 200 may cause active value 28 to close (46), e.g., by a sending a second signal to active valve 28. Active valve 28 may close in response to the second signal thereby preventing the flow of fluid through the lumen, such as drainage lumen 34.

Figure 5A:
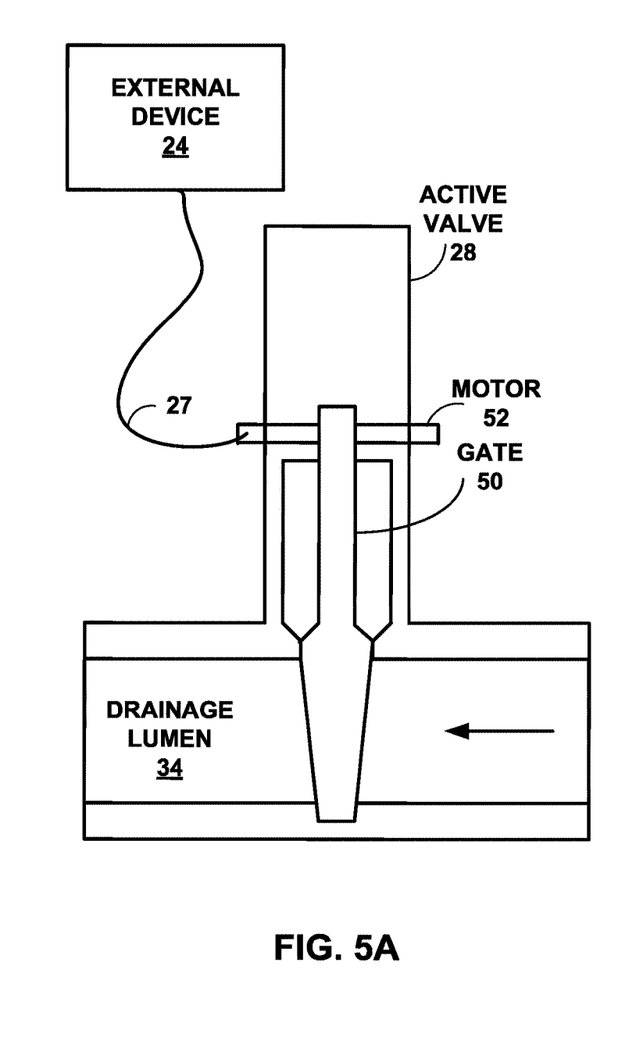
FIGS. 5A-5B are diagrams illustrating the operation of an example active valve of FIG. 1.
Figure 5B:
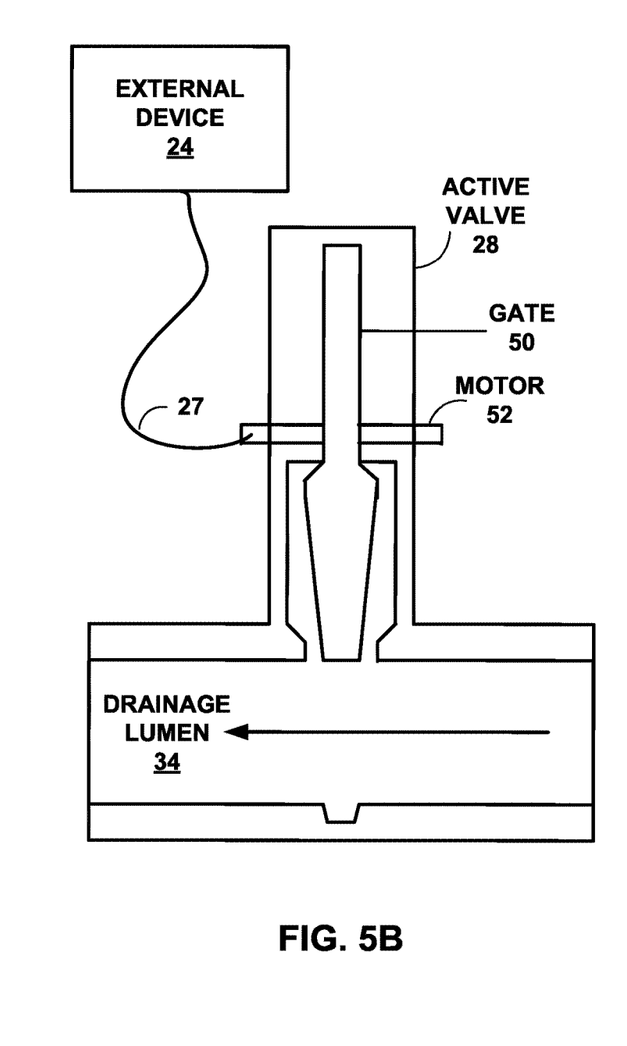

FIGS. 5A and 5B are conceptual diagrams of an example active valve located in or about drainage lumen 34 of elongated body 12 of catheter 10. In the example of FIG. 5A, active valve 28 is a gate valve having a motor 52 and gate 50. While active valve is a gate valve in this example, active valve may be a gate valve, a globe valve, a plug valve, a ball valve, a butterfly valve, a diaphragm valve, a pinch valve, a needle valve or any type of valve that may enable the flow of a fluid through drainage lumen 34 when open and prevent the flow of the fluid through drainage lumen 34 when closed. In FIG. 5A, active valve 28 is closed, preventing the flow of a fluid, such as urine, through drainage lumen 34. In this example, gate 50 is positioned in drainage lumen 34 blocking the flow of the fluid through drainage lumen 34. By active valve being closed, bladder pressure may build up in a patient, as urine is held in the bladder and is not flowing through drainage lumen 34.

External device 24 is connected to motor 52 of active valve 28. In response to determining that a first condition occurred, control circuitry 210 of external device 24 may send a first signal over connection 27 to motor 52 of active valve 28 to open gate 50. Motor 52 may then raise gate 50 in response to receiving the first signal. Connection 27 can include a wired connection, an optical connection or a wireless connection.

In the example of FIG. 5B, active valve 28 is in the open position, enabling the flow of fluid, such as urine, through drainage lumen 34 and, for example, out of a bladder of a patient to a collection bag or the like when elongated body 12 is positioned such that proximal end 12B is positioned in the bladder. In this example, gate 50 is raised and is not positioned in drainage lumen 34 thereby enabling the flow of the fluid through drainage lumen 34. As active valve was closed previously causing the build up of bladder pressure, the flow of fluid, such as urine, through drainage lumen 34 may be faster than the flow otherwise would have been. This may decrease transit time of the fluid through drainage lumen 34.

In response to determining that a second condition has occurred, control circuitry 510 of external device 24 may send a second signal over connection 27 to motor 52 to close gate 50. Motor 52 may then close gate 50 in response to receiving the second signal bringing the state of active valve 28 back to the example of FIG. 5A.

The techniques of the present disclosure may improve the accuracy of the sensing of parameters of a substance of interest at a distal portion of a catheter or distal to a distal end of the catheter. The reduction of the transit time of a fluid, such as urine through the relatively porous material of the elongated body of a catheter due to the use of an active valve, may decrease the amount of the material of interest that may permeate the porous material resulting in a more accurate measurement. Additionally, the use of a check valve may further improve the accuracy of the sensing of parameters by prohibiting the mixing of air with the fluid in a lumen of the catheter.

The techniques described in this disclosure, including those attributed to sensor 20, sensor 21, processing circuitry 200, communication circuitry 206, control circuitry 210 and UI 204 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure includes the following examples.

EXAMPLE 1

A catheter comprising: an elongated body defining an injection lumen, a drainage lumen, and an inflation lumen, the elongated body comprising a proximal portion and a distal portion; an anchoring member positioned on the proximal portion of the elongated body, the anchoring member being fluidically coupled to the inflation lumen; and an active valve positioned in or about the drainage lumen, wherein the active valve is configured to move between a closed state in which, when a proximal end of the elongated body is positioned in a bladder of a patient, the active valve is configured to retain fluid in the bladder, and an open state in which the active valve enables drainage of fluid from the bladder via the drainage lumen.

EXAMPLE 2

The catheter of example 1, further comprising a check valve configured to prevent air from flowing through the drainage lumen.

EXAMPLE 3

The catheter of example 1 or 2, further comprising control circuitry, the control circuitry being configured to determine a condition has occurred and in response to determining the condition has occurred to control the active valve to open the active valve.

EXAMPLE 4

The catheter of example 3, wherein the condition is based on a time.

EXAMPLE 5

The catheter of example 4, wherein the time is one of a time the catheter was inserted into a patient, a last time the active valve was closed, or a last time the active valve was opened.

EXAMPLE 6

The catheter of any combination of examples 3-5, wherein the condition is based on sensor data.

EXAMPLE 7

The catheter of example 6, wherein the sensor data comprises data indicative of a bladder pressure.

EXAMPLE 8

The catheter of any combination of examples 1-7, further comprising a sensor configured to sense the sensor data indicative of a condition of the bladder.

EXAMPLE 9

The catheter of any combination of examples 3-8, wherein the condition is based on user input.

EXAMPLE 10

The catheter of example 3, wherein the condition is a first condition and the control circuitry is further configured to: determine a second condition has occurred; and in response to determining the second condition has occurred, control the active valve to close the active valve to retain fluid in the bladder of the patient.

EXAMPLE 11

The catheter of example 10, wherein the second condition is based on one of a time the active valve was last opened, sensor data or user input.

EXAMPLE 12

The catheter of any combination of examples 1-11, wherein the injection lumen is configured to transport fluid from the distal portion of the elongated body to a fluid opening on the proximal portion of the elongated body.

EXAMPLE 13

The catheter of any combination of examples 1-12, wherein the drainage lumen is configured to transport fluid from the proximal portion of the elongated body to a fluid opening on the distal portion of the elongated body.

EXAMPLE 14

The catheter of any combination of examples 1-13, further comprising a sensor positioned on the distal portion of the elongated body or distal to a distal end of the elongated body.

EXAMPLE 15

The catheter of example 14, further comprising a hub at the distal end of the elongated body, wherein the sensor is positioned on the hub.

EXAMPLE 16

The catheter of example 14, further comprising a hub at the distal end of the elongated body, wherein the sensor is positioned distal to the hub.

EXAMPLE 17

The catheter of any combination of examples 14-16, wherein the sensor is a dissolved oxygen sensor.

EXAMPLE 18

A method comprising: determining, by control circuitry, a condition has occurred; and in response to determining the condition has occurred, control an active valve of a catheter to open the active valve, the catheter comprising: an elongated body defining an injection lumen, a drainage lumen, and an inflation lumen, the elongated body comprising a proximal portion and a distal portion; an anchoring member positioned on the proximal portion of the elongated body, the anchoring member being fluidically coupled to the inflation lumen; and the active valve positioned in or about the drainage lumen, wherein the active valve is configured to move between a closed state in which, when a proximal end of the elongated body is positioned in a bladder of a patient, the active valve is configured to retain fluid in the bladder, and the open state in which the active valve enables the drainage of fluid from the bladder of the patient via the drainage lumen.

EXAMPLE 19

The method of example 18, wherein determining the condition has occurred comprises receiving sensor data indicative of a bladder condition from a sensor and determining the condition has occurred based on the sensor data.

EXAMPLE 20

The method of example 19, wherein the sensor data comprises bladder pressure data.

EXAMPLE 21

The method of any combination of examples 18-20, wherein determining whether the condition has occurred comprises determining the condition has occurred based on a time.

EXAMPLE 22

The method of example 21, wherein the time is one of a time the catheter was inserted in a patient, a last time the active valve was closed, or a last time the active valve was opened.

EXAMPLE 23

The method of any combination of examples 18-22, wherein determining whether the condition has occurred comprises receiving user input and determining the condition has occurred based on the user input.

EXAMPLE 24

The method of any combination of examples 18-23, wherein the catheter further comprises: a hub connected to the distal portion of the elongated body; and a sensor positioned on the hub or distal to the hub.

EXAMPLE 25

The method of example 24, wherein the sensor is a dissolved oxygen sensor.

EXAMPLE 26

The method of any combination of examples 18-25, wherein the catheter is a Foley catheter.

EXAMPLE 27

The method of example 18-26, wherein the condition is a first condition and the method further comprises: determining, by the control circuitry, a second condition has occurred; and in response to determining the second condition has occurred, controlling the active valve to close the active valve to retain fluid in the bladder of the patient.

EXAMPLE 28

The method of example 27, wherein the second condition is based on one of a time the active valve was last opened, sensor data or user input.

EXAMPLE 29

A Foley catheter comprising: an elongated body defining an injection lumen, a drainage lumen, and an inflation lumen, the elongated body comprising a proximal portion and a distal portion; an anchoring member positioned on the proximal portion of the elongated body and fluidically coupled to the inflation lumen; a sensor positioned on the distal portion of the elongated body or distal to a distal end of the elongated body, the sensor configured to sense a substance of interest; a check valve positioned in or about the drainage lumen, the check valve being configured to prevent air from flowing through the drainage lumen; and an active valve positioned in or about the drainage lumen, the active valve being configured to move between a closed state in which, when a proximal end of the elongated body is positioned in a bladder of the patient, the active valve is configured to retain fluid in the bladder, and an open state in which the active valve enables drainage of the fluid from the bladder via the drainage lumen.

EXAMPLE 30

The Foley catheter of example 29, the sensor comprises a dissolved gas sensor and the dissolved gas sensor comprises a dissolved oxygen sensor.

Various examples have been described. These and other examples are within the scope of the following claims.

What is claimed is:

1. A catheter comprising:
   an elongated body defining an injection lumen, a drainage lumen, and an inflation lumen, the elongated body comprising a proximal portion and a distal portion;
   an anchoring member positioned on the proximal portion of the elongated body, the anchoring member being fluidically coupled to the inflation lumen;
   an active valve positioned in or about the drainage lumen, wherein the active valve is configured to move between a closed state in which, when a proximal end of the elongated body is positioned in a bladder of a patient, the active valve is configured to retain fluid in the bladder, and an open state in which the active valve enables drainage of the fluid from the bladder via the drainage lumen; and
   control circuitry configured to:
      receive an indication to measure a first parameter associated with the fluid from the bladder;
      receive data from a first sensor, wherein the first sensor is coupled to the catheter and configured to sense a second parameter associated with the fluid that is different than the first parameter;
      based on the indication and on the data from the first sensor meeting a threshold value, cause the active valve to be in the open state;
      receive second data from a second sensor coupled to the catheter and configured to sense the first parameter associated with the fluid;
      receive additional data from the first sensor; and
      based on the additional data from the first sensor meeting an additional threshold value, control the active valve to be in the closed state.

2. The catheter of claim 1, further comprising a check valve configured to prevent air from flowing through the drainage lumen.

3. The catheter of claim 1, wherein the second parameter comprises a time.

4. The catheter of claim 3, wherein the data is associated with an initial time at which the catheter was inserted into the patient, a last time the active valve was closed, or a last time the active valve was opened.

5. The catheter of claim 1, wherein the second parameter comprises a pressure of the fluid or a flow rate of the fluid.

6. The catheter of claim 1, wherein the data comprises pressure sensor data indicative of a bladder pressure, and wherein the threshold value comprises a first predetermined bladder pressure value and the additional threshold value comprises a second predetermined bladder pressure value that is less than the first predetermined bladder pressure value.

7. The catheter of claim 1, wherein the indication comprises user input, and wherein the first parameter comprises an amount of oxygen in the fluid.

8. The catheter of claim 1, wherein the additional data comprises a time the active valve was last opened or user input.

9. The catheter of claim 1, wherein the injection lumen is configured to transport an additional fluid from the distal portion of the elongated body to a fluid opening on the proximal portion of the elongated body.

10. The catheter of claim 9, wherein the additional fluid is transported to the bladder of the patient when the active valve is in the closed state, and wherein the second parameter is based on a mixture of the fluid and the additional fluid.

11. The catheter of claim 1, wherein the drainage lumen is configured to transport the fluid from the proximal portion of the elongated body to a fluid opening on the distal portion of the elongated body.

12. The catheter of claim 1, wherein the second sensor is positioned on the distal portion of the elongated body or distal to a distal end of the elongated body.

13. The catheter of claim 1, further comprising a hub at a distal end of the elongated body, wherein the second sensor is positioned on the hub.

14. The catheter of claim 1, further comprising a hub at a distal end of the elongated body, wherein the second sensor is positioned distal to the hub.

15. The catheter of claim 1, wherein the second sensor is a dissolved oxygen sensor.

16. A method comprising:
   receiving, by control circuitry, an indication to measure a first parameter associated with fluid from a bladder of a patient;
   receiving, by the control circuitry, data from a first sensor, wherein the first sensor is configured to sense a second parameter associated with the fluid that is different than the first parameter;
   based on the indication and on the data from the first sensor meeting a predetermined value,
   controlling, by the control circuitry, an active valve of a catheter to be in an open state, the catheter comprising:
      an elongated body defining an injection lumen, a drainage lumen, and an inflation lumen, the elongated body comprising a proximal portion and a distal portion;
      an anchoring member positioned on the proximal portion of the elongated body, the anchoring member being fluidically coupled to the inflation lumen; and
      the active valve positioned in or about the drainage lumen, wherein the active valve is configured to move between a closed state in which, when a proximal end of the elongated body is positioned in the bladder of the patient, the active valve is configured to retain the fluid in the bladder, and the open state in which the active valve enables the drainage of the fluid from the bladder of the patient via the drainage lumen; and
   receiving, by the control circuitry, second data from a second sensor coupled to the catheter and configured to sense the first parameter associated with the fluid;
   receiving, by the control circuitry, additional data from the first sensor; and
   based on the additional data from the first sensor meeting an additional predetermined value, controlling, by the control circuitry, the active valve to be in the closed state.

17. The method of claim 16, wherein the second parameter comprises a pressure of the fluid or a flow rate of the fluid.

18. The method of claim 16, wherein the first sensor is coupled to the catheter, and wherein the data is indicative of a bladder pressure, and wherein the predetermined value comprises a first bladder pressure value and the additional predetermined value comprises a second bladder pressure value that is lower than the first bladder pressure value.

19. The method of claim 16, wherein the second parameter comprises a time.

20. The method of claim 19, wherein the data is associated with an initial time the catheter was inserted in the patient, a last time the active valve was closed, or a last time the active valve was opened.

21. The method of claim 16, wherein receiving the indication comprises receiving user input, and wherein the first parameter comprises an amount of dissolved oxygen in the fluid.

22. The method of claim 16, wherein the catheter further comprises a hub connected to the distal portion of the elongated body, and wherein the second sensor is positioned on the hub or distal to the hub.

23. The method of claim 22, wherein the second sensor is a dissolved oxygen sensor.

24. The method of claim 16, wherein the catheter is a Foley catheter.

25. The method of claim 16, wherein the additional data comprises a time the active valve was last opened or user input.

26. The method of claim 16, wherein the injection lumen is configured to transport an additional fluid from the distal portion of the elongated body to a fluid opening on the proximal portion of the elongated body.

27. The method of claim 26, wherein the additional fluid is transported to the bladder of the patient when the active valve is in the closed state, and wherein the second parameter is based on a mixture of the fluid and the additional fluid.

28. A Foley catheter comprising:
an elongated body defining an injection lumen, a drainage lumen, and an inflation lumen, the elongated body comprising a proximal portion and a distal portion;
an anchoring member positioned on the proximal portion of the elongated body and fluidically coupled to the inflation lumen;
a first sensor positioned on the distal portion of the elongated body or distal to a distal end of the elongated body, the first sensor configured to sense a first parameter associated with a fluid from a bladder of a patient;
a check valve positioned in or about the drainage lumen, wherein the check valve prevents air from flowing through the drainage lumen;
an active valve positioned in or about the drainage lumen, the active valve being configured to move between a closed state in which, when a proximal end of the elongated body is positioned in the bladder of the patient, the active valve is configured to retain the fluid in the bladder, and an open state in which the active valve enables drainage of the fluid from the bladder via the drainage lumen; and
control circuitry configured to:
receive an indication to measure the first parameter associated with the fluid from the bladder;
receive data from a second sensor, wherein the second sensor is coupled to the Foley catheter and configured to sense a second parameter associated with the fluid that is different than the first parameter;
based on the indication and on the data from the second sensor meeting a threshold value, cause the active valve to be in the open state;
receive second data from the first sensor coupled to the catheter and configured to sense the first parameter associated with the fluid;
receive additional data from the second sensor; and
based on the additional data from the second sensor meeting an additional threshold value, control the active valve to be in the closed state.

29. The Foley catheter of claim 28, wherein the first sensor comprises a dissolved gas sensor and the dissolved gas sensor comprises a dissolved oxygen sensor.

30. The Foley catheter of claim 28, wherein the injection lumen is configured to transport an additional fluid from the distal portion of the elongated body to a fluid opening on the proximal portion of the elongated body when the active valve is in the closed state, and wherein the second parameter is based on a mixture of the fluid and the additional fluid.

* * * * *